US008308923B2

(12) United States Patent
Chen

(10) Patent No.: US 8,308,923 B2
(45) Date of Patent: Nov. 13, 2012

(54) BIOSENSOR STRIP

(75) Inventor: Chun-Yu Chen, Taipei (TW)

(73) Assignee: R3DStar Biomedical Corp. (TW)

( * ) Notice: Subject to any disclaimer, the term of this patent is extended or adjusted under 35 U.S.C. 154(b) by 116 days.

(21) Appl. No.: 12/770,515

(22) Filed: Apr. 29, 2010

(65) Prior Publication Data
US 2011/0266150 A1 Nov. 3, 2011

(51) Int. Cl.
G01N 27/327 (2006.01)
(52) U.S. Cl. ...................... 204/403.1; 435/25
(58) Field of Classification Search ............ 204/403.01–403.15; 205/792; 435/10, 287, 9, 14, 25, 435/26, 40.5
See application file for complete search history.

(56) References Cited

U.S. PATENT DOCUMENTS

| 5,120,420 | A | * | 6/1992 | Nankai et al. | 204/403.11 |
| 6,004,441 | A | * | 12/1999 | Fujiwara et al. | 204/403.14 |
| 6,299,757 | B1 | * | 10/2001 | Feldman et al. | 205/775 |
| 2003/0196894 | A1 | * | 10/2003 | Cai et al. | 204/403.01 |

* cited by examiner

Primary Examiner — J. Christopher Ball

(57) ABSTRACT

The present invention discloses a biosensor strip, which comprises: a base plate layer defining a first strip end and a second strip end; a conductive layer being disposed on the base plate layer and partitioned into at least two electrode paths; a reagent containing layer being disposed on the conductive layer and comprising a first through hole that is located at the first strip end and for accommodating a reagent solution, wherein the reagent solution comprises matrix, redox mediator, enzyme, surfactant, and a buffer solution; a channel forming layer being disposed on the reagent containing layer and comprising a gap portion that is located at the first strip end; and a cover layer being disposed on the channel forming layer and comprising a second through hole that exposes the partial area of the gap portion of the channel forming layer.

3 Claims, 6 Drawing Sheets

BIOSENSOR STRIP

BACKGROUND OF THE INVENTION

1. Field of the Invention

The present invention relates to a biosensor strip, and more particularly to a biosensor strip which can detect the concentration of a specific ingredient in the trace amount of a fluid sample.

2. Description of the Prior Art

A biosensor can detect the concentration of a specific analyte in a fluid sample, and the use of different reagents can detect a lot of kinds of analytes. In recent years, owing to people paying more and more attention to health, biosensors are equipped in most hospitals and families to detect the concentration of a specific ingredient in a human body at any time.

Biosensors are widely used for detecting the concentration of blood glucose. Blood glucose is a very important material for maintaining homeostasis in a biological body, if the functions of enzymes related to the control of the concentration of blood glucose, such as insulin, are not enough, diabetes may happens when the concentration of blood glucose being raised to a particular level. If the concentration of blood glucose is below the normal range, patients can suffer from unconsciousness and lowered blood pressure which may even result in death.

A biosensor is composed of a biosensor strip and a measuring device. After a blood sample reacting with a reagent in the biosensor strip, electrochemical or optical signals are produced. Then the measuring device is used for detecting the signals generated in the biosensor strip to determine the concentration of a specific analyte.

In order to obtain a blood sample of a patient, a syringe is pricked into the skin of the patient. The sample channel of a conventional biosensor strip is often larger, thus it requires more than 2 micro liter of the blood sample to get into the biosensor strip and to be detected. However, it may cause the patient's wound uncomfortable to obtain such volume of blood, and it is painful for the patient need to analyze his blood usually. In fact, it requires only less than 0.2 micro liter of blood to react with the reagent in the biosensor strip and detect the concentration of a specific analyte. Thus the conventional biosensor strip has improvement spaces.

Additionally, when a conventional biosensor strip is used for detecting a blood sample, it usually spends a period of time for the blood sample to completely get into the sample channel of the biosensor strip, and then the blood sample can react with the reagent, thus a round of measurement has to take a long time. In view of this, it is necessary to provide an improved biosensor strip for shortening the time of the blood sample getting into the sample channel.

Furthermore, although the composition of the reagent used in the conventional biosensor strip has been improved constantly, error value in some degrees is still exists in the results of detection, thus providing a reagent with improved composition to decrease error value is an important subject matter.

SUMMARY OF THE INVENTION

In view of the above shortcomings of the prior art, the inventor of the present invention resorted to past experience, imagination, and creativity, performed experiments and researches repeatedly, and eventually devised the present invention—a biosensor strip.

The major objective of the present invention is to provide a biosensor strip, which has a hydrophilic cover layer and a second through hole thereon as a vent opening so as to promote the speed of a fluid sample getting into the sample channel and shorten the measuring time.

Another objective of the present invention is to provide the biosensor strip, which has a reagent solution with improved composition to increase the reacting rate and decrease error value.

Further objective of the present invention is to provide the biosensor strip, which reduces the volume of the sample channel so as to decrease the use of the blood sample and diminish the pain on the patient to the lowest level.

Consequently, the present invention provides a biosensor strip, which comprises: a base plate layer defining a first strip end and a second strip end; a conductive layer being disposed on the base plate layer and partitioned into at least two electrode paths, wherein the two electrode paths are insulated from each other and the conductive layer comprises a conductive contact at the second strip end; a reagent containing layer being disposed on the conductive layer and comprising a first through hole that is located at the first strip end and for accommodating a reagent solution, wherein the first through hole exposes the partial area of the two electrode paths simultaneously and the reagent solution comprises matrix, redox mediator, enzyme, surfactant, and a buffer solution; a channel forming layer being disposed on the reagent containing layer and comprising a gap portion that is located at the first strip end, wherein the gap portion exposes the first through hole; and a cover layer being disposed on the channel forming layer and comprising a second through hole that exposes the partial area of the gap portion of the channel forming layer; wherein a sample channel is formed with the gap portion by placing the channel forming layer between the reagent containing layer and the cover layer, and the second through hole is as a vent opening, so as to increase the speed of a fluid sample getting into the sample channel.

DETAILED DESCRIPTION OF THE PREFERRED EMBODIMENTS

To achieve the foregoing objectives and effects, the inventors improve the structure of the conventional biosensor strip and adjust the composition of the reagent solution, thus achieving a biosensor strip of the present invention. Hereinafter, the biosensor strip according to a first and a second preferred embodiment of the present invention are described in detail to illustrate the structure and spirit of the present invention.

Figure 1:
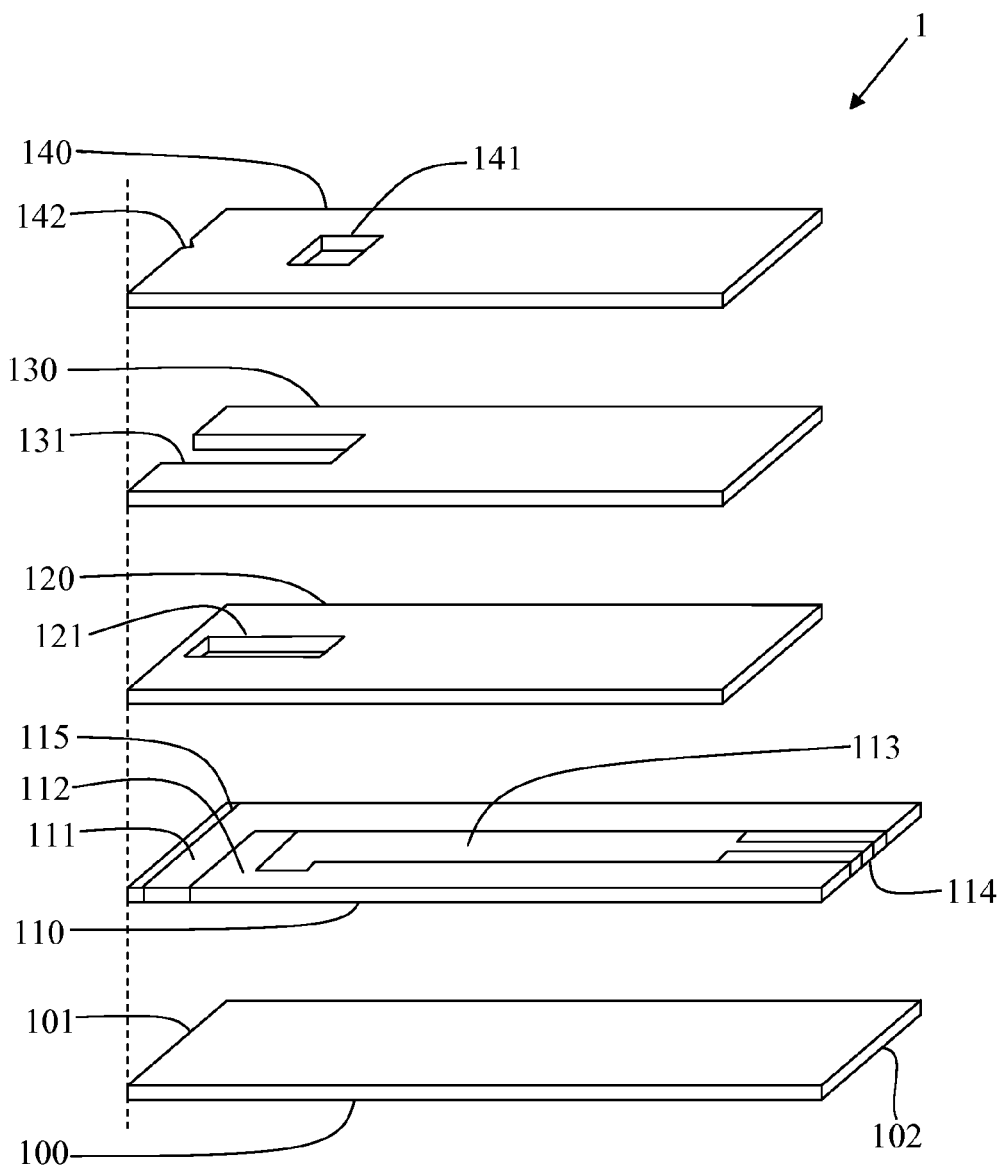
FIG. 1 is an exploded diagram of a biosensor strip according to a first preferred embodiment of the present invention.
Figure 2:
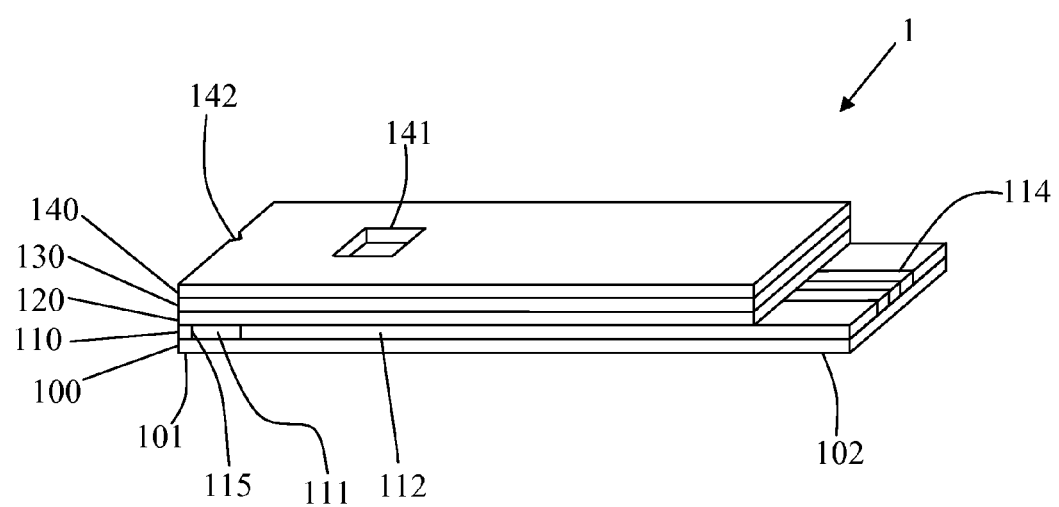
FIG. 2 is a perspective assembly diagram of the biosensor strip according to the first preferred embodiment of the present invention.
Figure 3:
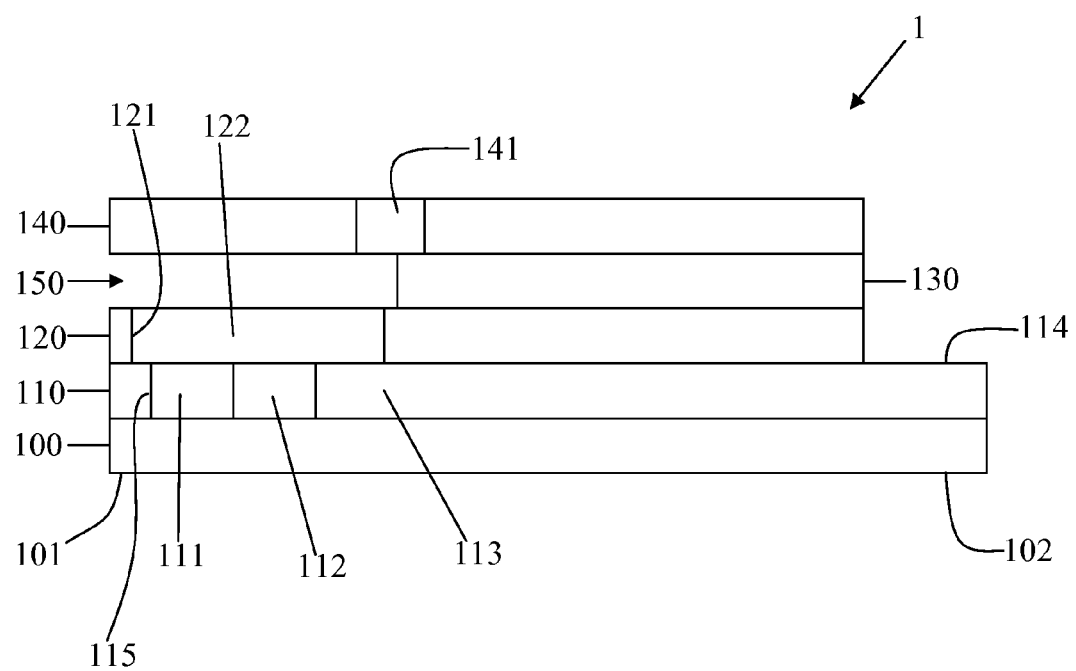
FIG. 3 is a sectional diagram of the biosensor strip according to the first preferred embodiment of the present invention.

Referring to FIG. 1, FIG. 2 and FIG. 3 at the same time, FIG. 1 is the exploded diagram of the biosensor strip according to the first preferred embodiment of the present invention, FIG. 2 is the perspective assembly diagram of the biosensor strip according to the first preferred embodiment of the present invention, FIG. 3 is the sectional diagram of the biosensor strip according to the first preferred embodiment of the present invention. The biosensor strip 1 includes a base plate layer 100, a conductive layer 110, a reagent containing layer 120, a channel forming layer 130, and a cover layer 140.

The base plate layer 100 defines a first strip end 101 and a second strip end 102.

The conductive layer 110 is formed by coating a conductive material on the base plate layer 100, and partitioned into three electrode paths 111, 112 and 113 which are insulated from each other. The conductive layer 110 includes a conductive contact 114 at the second strip end 102. In the first preferred embodiment of the present invention, the conductive layer 110 is made of gold.

The reagent containing layer 120 is disposed on the conductive layer 110 and includes a first through hole 121 that is located at the first strip end 101 and for accommodating a reagent solution 122. The first through hole 121 exposes the partial area of the three electrode paths 111, 112 and 113 simultaneously. The reagent solution 122 includes matrix, redox mediator, enzyme, surfactant, and a buffer solution.

The channel forming layer 130 is disposed on the reagent containing layer 120 and includes a gap portion 131 that is located at the first strip end 101, wherein the gap portion 131 exposes the first through hole 121.

The cover layer 140 is disposed on the channel forming layer 130 and includes a second through hole 141 which exposes the partial area of the gap portion 131 of the channel forming layer 130. The cover layer 140 further includes an inlet notch 142 at the first strip end 101, wherein the inlet notch 142 can point out the position of the entrance of a sample channel 150 so as to increase the convenience of using the biosensor strip 1.

Wherein, the sample channel 150 is formed with the gap portion 131 by placing the channel forming layer 130 between the reagent containing layer 120 and the cover layer 140, and the second through hole 141 is as a vent opening, so as to increase the speed of a fluid sample getting into the sample channel 150. Additionally, owing to the volume of the sample channel 150 is decreased in the present invention, less than 1 micro liter of fluid sample can be used for detecting the concentration of a specific analyte.

In the foregoing of the first preferred embodiment, the conductive layer 110, the reagent containing layer 120, the channel forming layer 130, and the cover layer 140 are combined tightly to each other by a thin layer of colloid.

Additionally, the base plate layer 100, the reagent containing layer 120 and the channel forming layer 130 are made of an insulated material, which can be polyethylene terephthalate (PET). The cover layer 140 is made of an insulated and hydrophilic material. In the first preferred embodiment of the present invention, the material of the cover layer 140 is PET which is treated by KOH and has a hydrophilic property. Except PET, cover layer 140 can be made of a hydrophilic thin membrane or a hydrogel.

Furthermore, the detailed composition and content of the reagent solution 122 used in the first preferred embodiment of the present invention are described in the following. The material of the matrix is chitosan with the concentration of 2%~40%, and the matrix has the function of a binder. In practice, the matrix can be made of one or more than one materials selected from the group consisted of: chitosan, PEI, PEO, cellulose, and nafion. The material of the redox mediator is ferricyanide with the concentration of 20%~35%. In practice, the redox mediator may alternatively be ferrocyanide or hexaammineruthenium chloride. The material of the enzyme is glucose oxidase with the concentration of 4 U~8 U. In practice, glucose dehydrogenase can be the ingredient of the enzyme, and glucose dehydrogenase needs a coenzyme, such as NADH, to accomplish a dehydration reaction. The material of the surfactant is triton with a trace of concentration. The buffer solution is PBS, in practice, citric buffer may be the ingredient of the buffer solution.

Moreover, reagent solution 122 is accommodated in the first through hole 121 of the reagent containing layer 120 and contacted with the three electrode paths 111, 112 and 113, thus the three electrode paths 111, 112 and 113 can receive the current changes generated from the reaction between the fluid sample and the reagent solution and further can determine the concentration of a specific analyte. In the first preferred embodiment of the present invention, the first electrode path 111 is a working electrode and the second electrode path 112 is a counter electrode, wherein the working electrode is input a voltage of 0.1V~0.4V higher than the voltage of the counter electrode. With the difference of the voltage, the current changes resulted from the catalytic reactions under different redox potentials can be detected, and then the concentration of the specific analyte can further be measured. Besides, the third electrode path 113 can be left unused, and it also can be a second working electrode for detecting the concentration of the specific analyte repeatedly to increase the accuracy of the detection. The third electrode path 113 can further be a short-fill electrode which is used to ensure that the fluid sample get into the sample channel 150 completely, that is, after the short-fill electrode receives the signals of the current changes, the working electrode and the counter electrode carry out their works.

Moreover, the conductive layer 110 further includes a scribe line 115, which partition the first electrode path 111, for adjusting the area ratio of the first electrode path 111 and the second electrode path 112 exposed in the first through hole 121 of the reagent containing layer 120. In the first preferred embodiment, the area of the first electrode path 111 exposed in the first through hole 121 is the same as the area of the second electrode path 112 exposed in the first through hole 121 (as shown in the FIG. 3), and the width of the scribe line 115 is in the range of 50 μm~100 μm.

Figure 4:
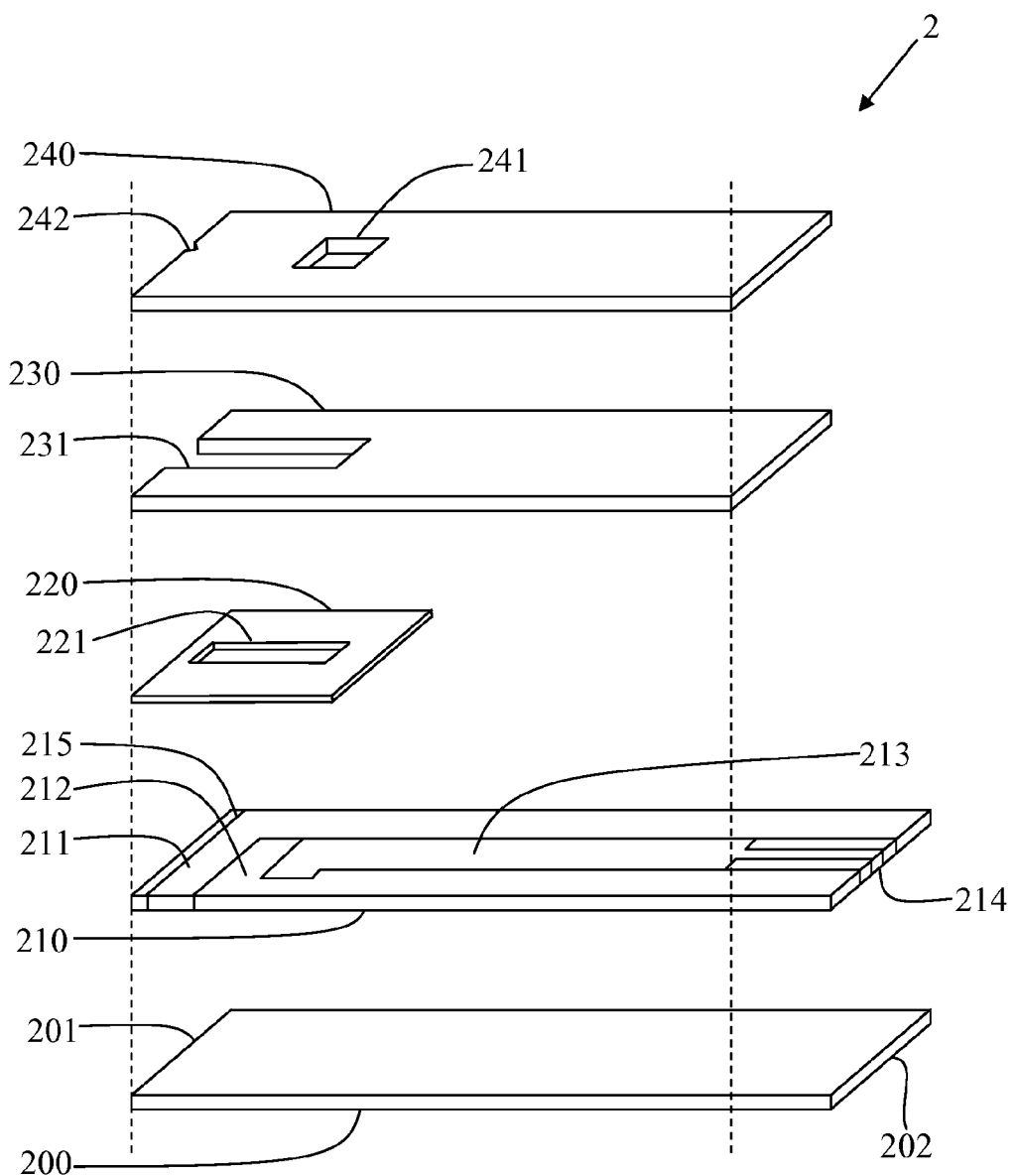
FIG. 4 is an exploded diagram of the biosensor strip according to a second preferred embodiment of the present invention.
Figure 5:
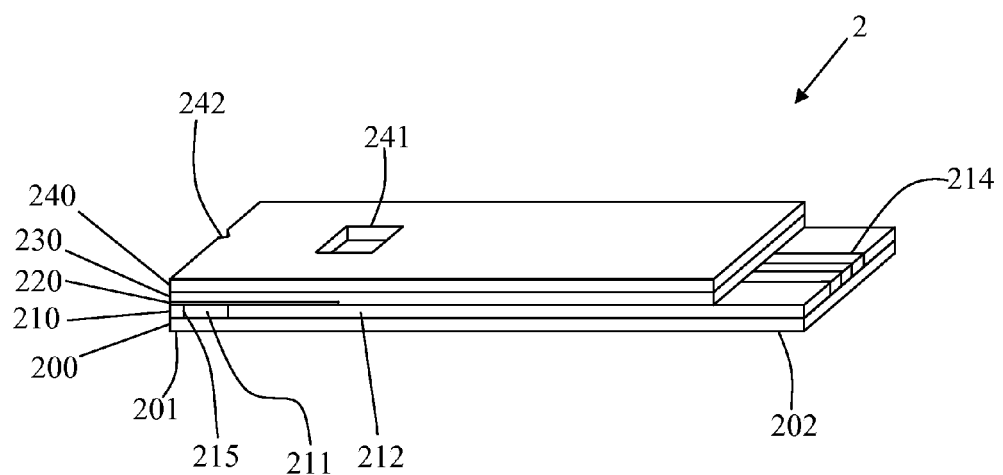
FIG. 5 is a perspective assembly diagram of the biosensor strip according to the second preferred embodiment of the present invention.
Figure 6:
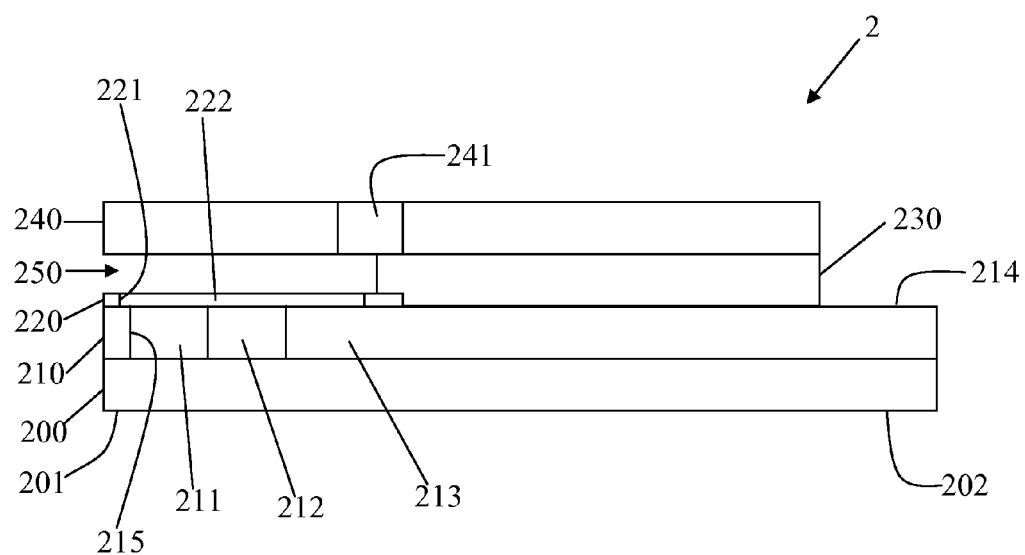
FIG. 6 is a sectional diagram of the biosensor strip according to the second preferred embodiment of the present invention.

Referring to FIG. 4, FIG. 5 and FIG. 6 at the same time, FIG. 4 is the exploded diagram of the biosensor strip according to the second preferred embodiment of the present invention, FIG. 5 is the perspective assembly diagram of the biosensor strip according to the second preferred embodiment of the present invention, FIG. 6 is the sectional diagram of the biosensor strip according to the second preferred embodiment of the present invention. The biosensor strip 2 includes a base plate layer 200, a conductive layer 210, an insulated thin layer 220, a channel forming layer 230, and a cover layer 240.

The base plate layer 200 defines a first strip end 201 and a second strip end 202.

The conductive layer 210 is formed by coating a conductive material on the base plate layer 200, and partitioned into three electrode paths 211, 212 and 213 which are insulated from each other. The conductive layer 210 includes a conductive contact 214 at the second strip end 202. In the second preferred embodiment of the present invention, the conductive layer 210 is made of gold.

The insulated thin layer 220 has an area smaller than the area of the conductive layer 210 and is disposed on the conductive layer 210 at the first strip end 201, and the insulated thin layer 220 includes a first through hole 221 that is located at the first strip end 201 and for accommodating a reagent solution 222. The first through hole 221 exposes the partial area of the three electrode paths 211, 212 and 213 simultaneously. The reagent solution 222 includes matrix, redox mediator, enzyme, surfactant, and a buffer solution.

The channel forming layer 230 is disposed on the conductive layer 210 and the insulated thin layer 220 and includes a gap portion 231 that is located at the first strip end 201, wherein the gap portion 231 exposes the first through hole 221.

The cover layer 240 is disposed on the channel forming layer 230 and includes a second through hole 241 which exposes the partial area of the gap portion 231 of the channel forming layer 230. The cover layer 240 further includes an inlet notch 242 at the first strip end 201, wherein the inlet notch 242 can point out the position of the entrance of a sample channel 250 so as to increase the convenience of using the biosensor strip 2.

Wherein, the sample channel 250 is formed with the gap portion 231 by placing the channel forming layer 230 between the insulated thin layer 220 and the cover layer 240, and the second through hole 241 is as a vent opening, so as to increase the speed of a fluid sample getting into the sample channel 250. Additionally, owing to the volume of the sample channel 250 is decreased in the present invention, less than 1 micro liter of fluid sample can be used for detecting the concentration of a specific analyte.

In the foregoing of the second preferred embodiment, the conductive layer 210, the channel forming layer 230, and the cover layer 240 are combined tightly to each other by a thin layer of colloid.

Additionally, the base plate layer 200 and the channel forming layer 230 are made of an insulated material, which can be polyethylene terephthalate (PET). The cover layer 240 is made of an insulated and hydrophilic material. In the second preferred embodiment of the present invention, the material of the cover layer 240 is PET which is treated by KOH and has a hydrophilic property. Except PET, cover layer 240 can be made of a hydrophilic thin membrane or a hydrogel.

Furthermore, the insulated thin layer 220 formed by a screen printing that disposes an insulated material on the conductive layer 210, and the insulated material is an insulated colloid.

Owing to the composition of the reagent solution 222 and the working principle of the electrode paths 211, 212 and 213 are in common with those of the first preferred embodiment, the details of these previously described comments are omitted herein.

By the detailed description of the overall structure and technical content of the present invention, the following advantages of the present invention can be derived:

The present invention employs the hydrophilic cover layer and the vent opening which can promote the speed of the liquid sample getting into the sample channel so as to decrease the measuring time.

The present invention improves the composition of the reagent solution which can increase the reaction efficiency and decrease the error value.

The present invention reduces the volume of the sample channel so as to decrease the use of the blood sample and diminish the pain on the patient to the lowest level.

The scribe line disposed on the conductive layer can adjust the area ratio of the electrode paths exposed in the first through hole of the reagent containing layer (or the insulated thin layer) so as to precisely control the area ratio of the reagent solution adheres on the different electrode paths and the coefficient of variation (CV) of the biosensor strip can be lowered greatly. This manner does not need the disposition of a plurality of through holes on the reagent containing layer, thus not only the biosensor strip of the present invention is easy to be manufactured but also the accuracy of the area ratio can be promoted greatly.

It should be understood that the embodiments of the present invention described herein are merely illustrative of the technical concepts and features of the present invention and are not meant to limit the scope of the invention. Those skilled in the art, after reading the present disclosure, will know how to practice the invention. Various variations or modifications can be made without departing from the spirit of the invention. All such equivalent variations and modifications are intended to be included within the scope of the invention.

As a result of continued thinking about the invention and modifications, the inventors finally work out the designs of the present invention that has many advantages as described above. The present invention meets the requirements for an invention patent, and the application for a patent is duly filed accordingly. It is expected that the invention could be examined at an early date and granted so as to protect the rights of the inventors.

What is claimed is:

1. A biosensor strip comprising:
a base plate layer defining a first strip end and a second strip end;
a conductive layer being disposed on the base plate layer and partitioned into a first electrode path, a second electrode path and a third second electrode path, wherein the three electrode paths are insulated from each other and the conductive layer comprises a conductive contact at the second strip end;
a reagent containing layer being disposed on the conductive layer and comprising a first through hole that is located near the first strip end and for accommodating a reagent solution, wherein the first through hole exposes a partial area of the three electrode paths simultaneously and the reagent solution comprises matrix, redox mediator, enzyme, surfactant, and a buffer solution;
a channel forming layer being disposed on the reagent containing layer and comprising a gap portion that is located at the first strip end, wherein the gap portion exposes the first through hole; and
a cover layer being disposed on the channel forming layer and comprising a second through hole that exposes a partial area of the gap portion of the channel forming layer;
an inlet notch located in the cover layer at the first strip end for indicating an entrance of a sample channel; and
at least one scribe line perpendicular to a direction connecting said first strip end and said second strip end, said at least one scribe line being configured for adjusting the area ratio of the first electrode path and the second electrode path exposed in the first through hole of the reagent containing layer;
wherein a sample channel is formed with the gap portion, the cover layer, the first and second through holes and the conductive layer by placing the channel forming layer between the reagent containing layer and the cover layer and the second through hole is as a vent opening so as to increase the speed of a fluid sample getting into the sample channel;
wherein the first electrode path is a working electrode and the second electrode path is a counter electrode, and third electrode path further be a short-fill electrode which is used to ensure that the fluid sample get into the sample channel completely;

wherein after the short-fill electrode receives the signals of the current changes, the working electrode and the counter electrode carry out their works.

2. The biosensor strip according to claim 1, wherein the conductive layer, the reagent containing layer, the channel forming layer, and the cover layer are combined tightly to each other by a thin layer of colloid.

3. The biosensor strip according to claim 1, wherein the base plate layer, the reagent containing layer and the channel forming layer are made of an insulated material and the cover layer is made of an insulated and hydrophilic material.

* * * * *